United States Patent [19]

Sammarco

[11] Patent Number: 5,718,705
[45] Date of Patent: Feb. 17, 1998

[54] INTERNAL FIXATION PLATE

[76] Inventor: Giacomo J. Sammarco, 430 W. Cliff La., Cincinnati, Ohio 45220

[21] Appl. No.: 683,039

[22] Filed: Jul. 16, 1996

[51] Int. Cl.$^6$ ..................................... A61B 17/58
[52] U.S. Cl. .................. 606/69; 606/60; 606/70; 606/72
[58] Field of Search ................. 606/60, 69, 70, 606/72

[56] References Cited

U.S. PATENT DOCUMENTS

| | | | |
|---|---|---|---|
| 4,903,691 | 2/1990 | Heinl | 606/70 |
| 4,905,679 | 3/1990 | Morgan | 606/70 |
| 5,364,398 | 11/1994 | Chapman et al. | 606/69 |

OTHER PUBLICATIONS

*Howmedica your orthopaedic resource*, 1992 Product Catalog, Chapter I.

*Primary Examiner*—Michael Buiz
*Assistant Examiner*—Daphna Shai
*Attorney, Agent, or Firm*—Frost & Jacobs

[57] ABSTRACT

A multi-purpose internal fixation plate for stabilization of fractured or broken bones. The fixation plate comprises a central hub portion with a plurality of radial, integral fingers extending therefrom and evenly spaced thereabout. The fixation plate is designed to be cut to size and to the desired configuration by the total or partial removal of one or more selected ones of the fingers. The fixation plate is further designed to be bent to the desired shape depending upon the application for which it is used. The hub portion and the fingers may be provided with appropriately configured apertures through which they can be screwed by surgical screws to the bone or bones to be stabilized. The fixation plate is made of any appropriate surgically compatible, bendable and cutable material, having sufficient strength.

23 Claims, 6 Drawing Sheets

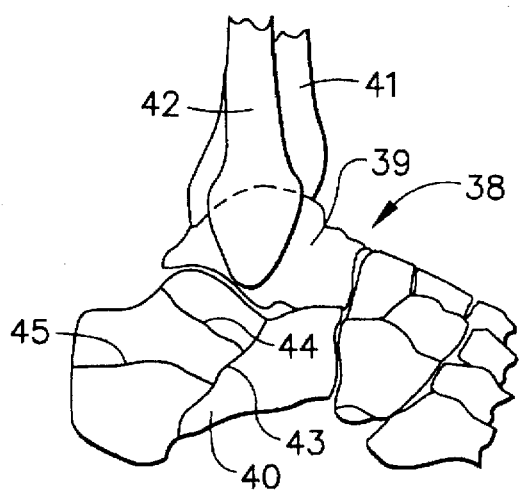
FIG. 12
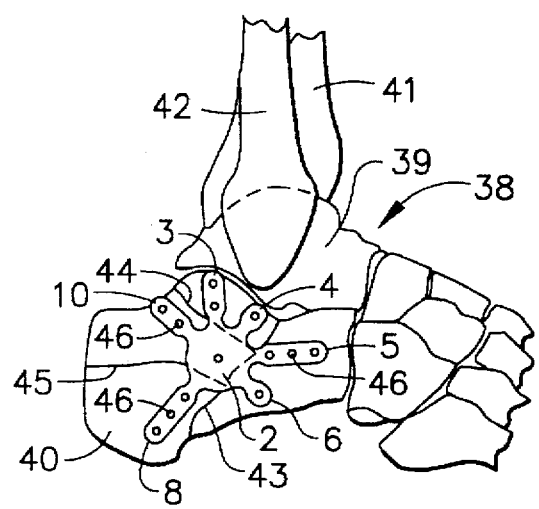
FIG. 13
FIG. 14
FIG. 15

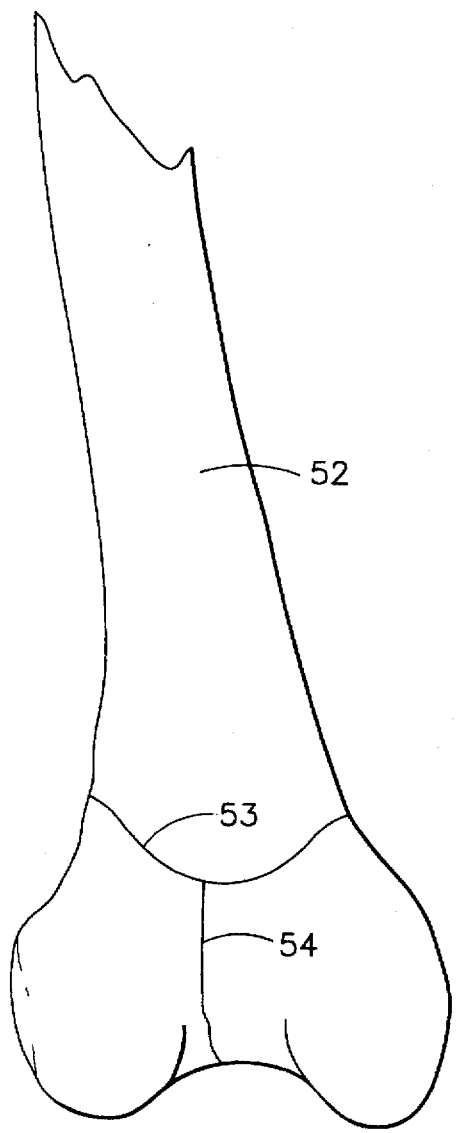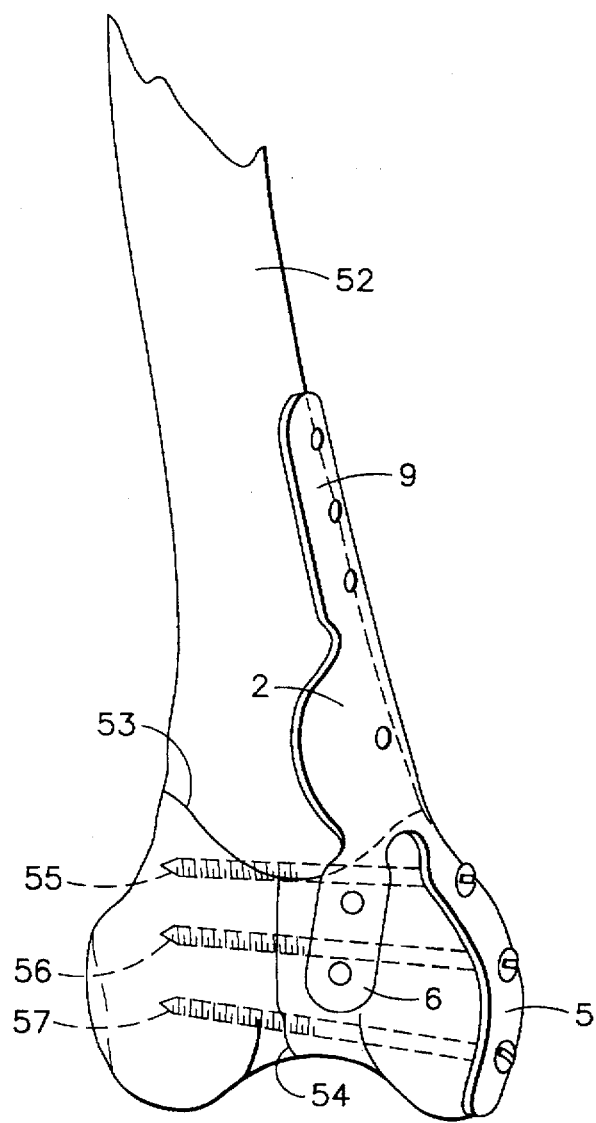
FIG. 16
FIG. 17

5,718,705

INTERNAL FIXATION PLATE

TECHNICAL FIELD

The invention relates to an internal fixation device for bone stabilization, and more particularly to such a device having a wide range of applications, being designed to be cut to the desired size and configuration and being adapted to be shaped by bending so as to properly fit the particular application for which it is to be used.

BACKGROUND ART

Internal fixation devices, frequently referred to as "bone plates" are well known in the art. These plates constitute endo-implants. They are not intended to replace fractured or broken bones or bone parts, but are used to stabilize bones which have been fractured, broken or severed as the result of trauma, deformity, surgery, or the like.

Prior art workers have devised a large number of internal fixation plates or bone plates, differing in size and configuration, and each being intended for a particular application. The choice of an appropriate bone plate depends upon a number of factors including the nature of the bone itself (shape, size, and the like), bone viability, and the nature of the fracture or break. Some of the most frequently encountered shapes include strap-shaped, H-shaped, Y-shaped, L-shaped and T-shaped. This list is exemplary only, and is by no means exhaustive. The fixation or bone plates are generally attached to the bones and/or bone fragments being stabilized by surgical screws. Alternatively, under some circumstances a fixation plate could be wired or banded in place. In many instances, the fixation plate may be provided with preformed holes through which the surgical screws extend. In some instances, prior art workers have so shaped the plate holes and the underside of the surgical screw heads, that, as the screws are tightened, they will provide compressive or pulling forces to bring the bone parts into intimate abutment.

The present invention is directed to a multi-purpose internal fixation plate which has a large number of fixation applications. As a result, it may be used to replace a large number of single-purpose fixation plates, cutting inventory costs. The internal fixation plate of the present invention is designed to be cut to the desired size and configuration, and is further designed to be bent to the desired shape. The cutting and bending steps may be accomplished prior to the operation, or during the operation. Preliminary cutting and bending could be performed before the operation and finalized during the operation. The internal fixation plate may be used with all of the well known surgical tools for this purpose, as well as some specialized tools, as will be set forth hereinafter. The fixation plate of the present invention may be made of any appropriate bendable and cutable material suitable for use in a surgical environment and having sufficient strength, as will be developed further hereinafter.

DISCLOSURE OF THE INVENTION

According to the invention there is provided a multi-purpose internal fixation plate for the stabilization of fractured or broken bones. The fixation plate is made of any appropriate cutable and bendable material characterized by being of sufficient strength for the purpose and by being compatible for use as an endo-implant. The fixation plate comprises a central hub portion having a plurality of radially oriented integral fingers extending therefrom and evenly spaced thereabout.

The fixation plate is designed to be cut to size and to the desired configuration depending upon the particular application for which it is being prepared. This is accomplished by the total or partial removal of one or more selected ones of the fingers. The fixation plate is further designed to be bent to the desired shape depending upon the particular application for which it is being prepared. These bending and shaping steps can be performed before or during an operation, or partly before and partly during an operation.

Both the hub portion and the fingers of the internal fixation plate may be provided with apertures through which it can be screwed with surgical screws to the bones or bone fragments to be stabilized. The fixation plate can be made in various sizes and will greatly reduce the heretofore required large inventory of variously shaped single-purpose fixation plates.

DESCRIPTION OF THE DRAWINGS

FIG. 12 is a lateral view of a comminuted calcaneal fracture.

FIG. 13 is a view similar to FIG. 12 and illustrates a fixation plate of the present invention applied to the reassembled calcaneus.

FIG. 14 is a posterior view of a comminuted fracture of the elbow.

FIG. 15 illustrates a fixation plate of the present invention applied to the fractured elbow of FIG. 14.

FIG. 16 is a posterior view illustrating a T-fracture of the femur at the knee.

FIG. 17 is a posterior view, similar to FIG. 18, and illustrating a fixation plate of the present invention applied to such a T-fracture.

DETAILED DESCRIPTION OF THE INVENTION

Figure 1:
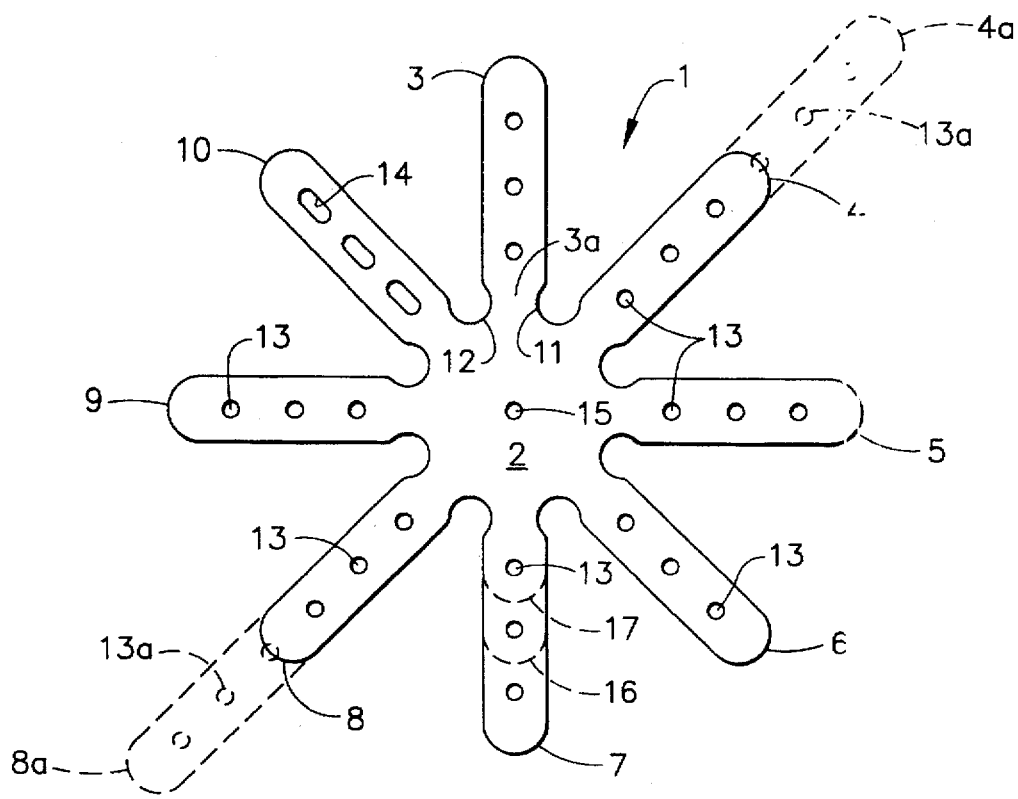
FIG. 1 is a plan view of an exemplary internal fixation plate of the present invention.

Reference is first made to FIG. 1 wherein an exemplary embodiment of the internal fixation plate of the present invention is generally indicated at 1. The plate 1 comprises a central hub portion 2 and a plurality of radially extending fingers 3–10. In the embodiment illustrated, the fingers are 8 in number. This number could be increased or decreased as desired. For most purposes, 8 fingers have proven to be adequate. It will be noted that each of the fingers 3–10 constitutes an integral one-piece part of the hub portion 2. It will further be noted that finger 3 narrows slightly (at 3a) as it joins the hub portion 2. While all of the fingers could be of continuous width throughout their length, the slight narrowing 3a makes the finger 3 a bit easier to bend adjacent to the hub 2. It will be noted that the peripheral edges 11 and 12, between fingers 3 and 4 and between fingers 3 and 10 are substantially circular. This configuration tends to eliminate stress raisers.

All of the fingers may be provided with a plurality of holes along their length for receipt of surgical screws. In FIG. 1, the finger holes are shown to be simple circular holes 13. While not so shown, it is often preferred that the holes 13 be countersunk so that the heads of the surgical screws do not extend much beyond the surfaces of the plate fingers. It is also within the scope of the invention to provide the plate fingers 3–10 with slots such as the slots 14 shown in Finger 10. Such slots enable adjustment of the bone with respect to the plate. In some instances, holes 13, or the slots 14, together with the underside of the heads of the surgical screws, may be so configured that, as each screw is tightened, it tends to push or pull the bone fragments into more intimate abutment. As indicated above, this is known in the art. It is also within the scope of the invention to provide the hub portion 2 of plate 1 with one or more screw holes. In FIG. 1, the hub is shown having one hole at 15.

The plate 1 may be made of any appropriate material so long as it is of sufficient strength; so long as it is capable of being cut and bent; and so long as it is compatible with the human body, so that it can be made into a permanent endo-implant.

At the present time and at the present state of the art, titanium, medical grade stainless steel and medical grade alloys may be used in the manufacture of the Plate 1. Titanium is presently preferred because it is more easily bent and shaped.

Currently, a great deal of work is being done in the field of materials such as polyglycolic acid which may, after a time, be absorbed by the body. When an absorbable material is developed which demonstrates sufficient strength and is capable of being cut and bent to shape, it would constitute an excellent material from which to form fixation plate 1 for some applications.

FIGS. 2 through 8 illustrate various bone plate configurations, all of which are made from the plate of FIG. 1. Thus, like parts have been given like index numerals.

Figure 2:
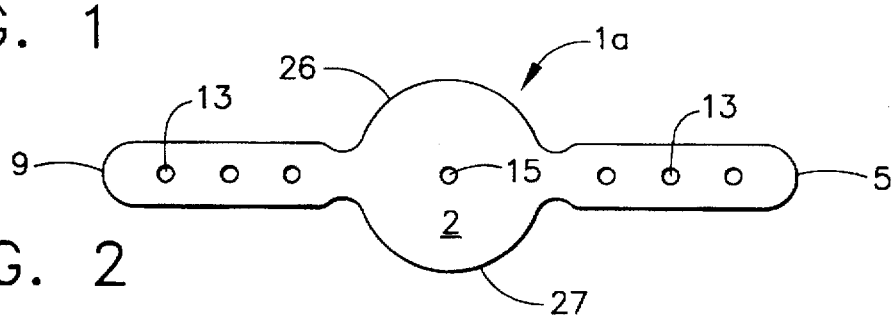
FIGS. 2 through 8 are exemplary configurations of the fixation plate which can be made from the fixation plate of FIG. 1.

FIG. 2 illustrates a fixation plate generally indicated at 1a made by the removal of fingers 3, 4, 6, 7, 8 and 10 from the plate of FIG. 1 to form a rectilinear strap-type fixation plate. In the illustrated embodiment, legs 5 and 9 remain as integral one-piece parts of hub portion 2. It will be understood that any diametrically opposed pair of the legs 3–10 of FIG. 1 could have been selected as the diametric pair of legs to remain attached to hub portion 2.

Figure 3:
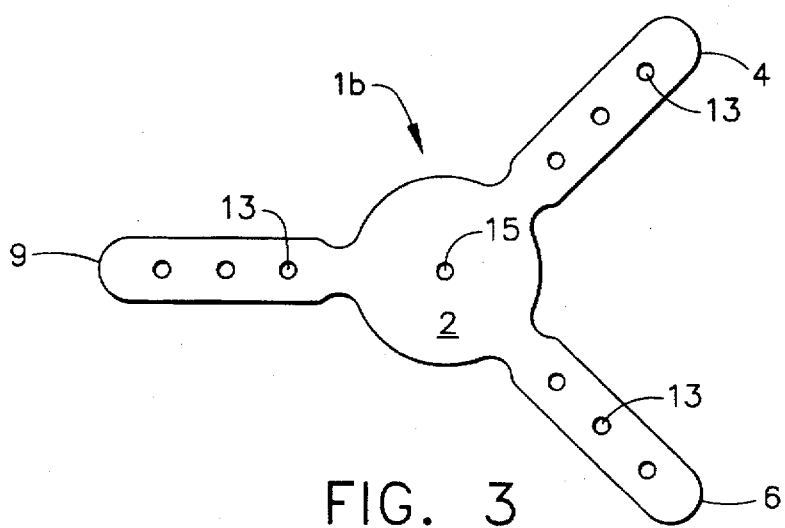

FIG. 3 illustrates another exemplary fixation plate 1b made by the removal of fingers 3, 5, 7, 8, and 10 from the plate 1 of FIG. 1, leaving fingers 4, 6 and 9 so as to form a Y-shaped fixation plate.

Figure 4:
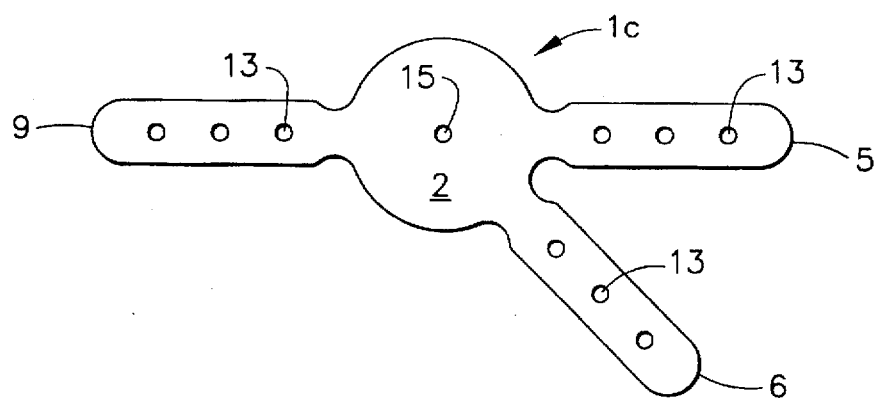

In FIG. 4, a fixation plate 1c is illustrated and it constitutes the result of the removal of fingers 3, 4, 7, 8, and 10 from the plate 1 of FIG. 1 so as to provide a plate having a skewed Y-shape.

Figure 5:
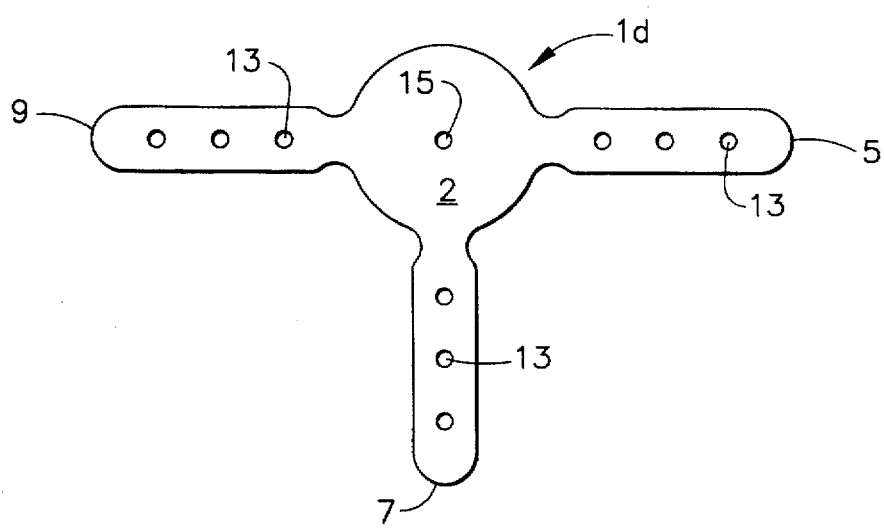

FIG. 5 illustrates a fixation plate 1d made by removing from plate 1 of FIG. 1 fingers 3, 4, 6, 8 and 10. This results in a T-shaped bone plate.

Figure 6:
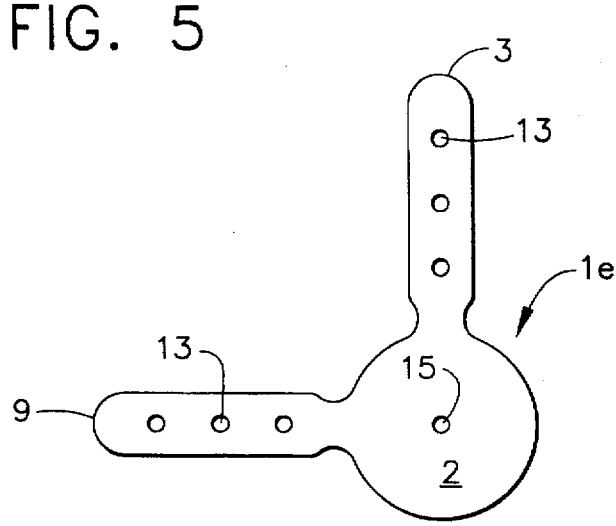

Similarly, the bone plate 1e of FIG. 6 is fabricated by removing the fingers 4, 5, 6, 7, 8 and 10 from the plate 1 of FIG. 1. This provides an L-shaped plate.

Figure 7:
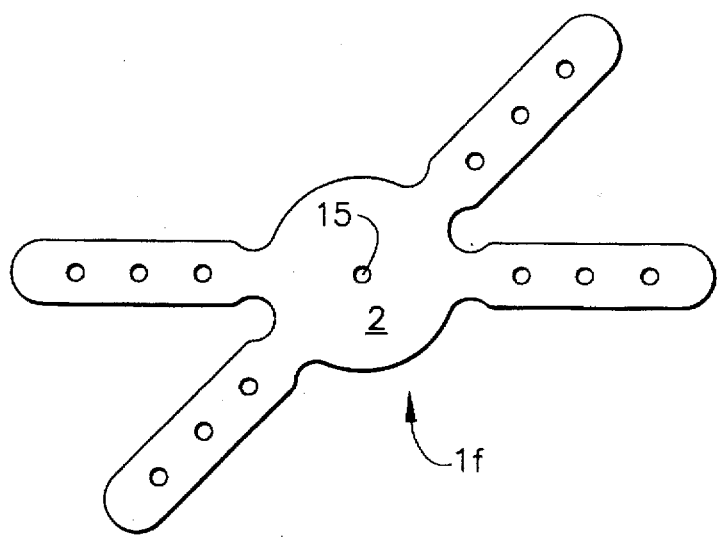

Fixation plate 1f of FIG. 7 results from the removal of fingers 3, 6, 7 and 10 from plate 1 of FIG. 1. This results in a substantially H-shaped fixation plate.

Figure 8:
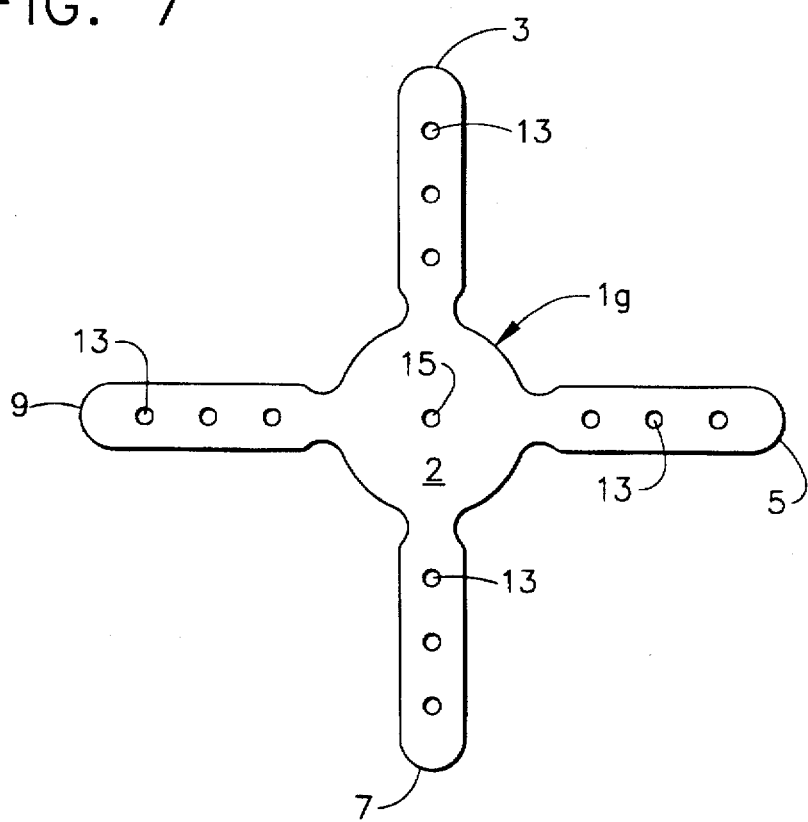
Figure 9:
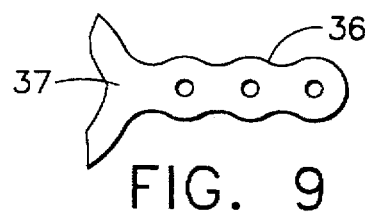
FIG. 9 is a fragmentary view of another type of finger which may be provided on the fixation plate of FIG. 1.
Figure 10:
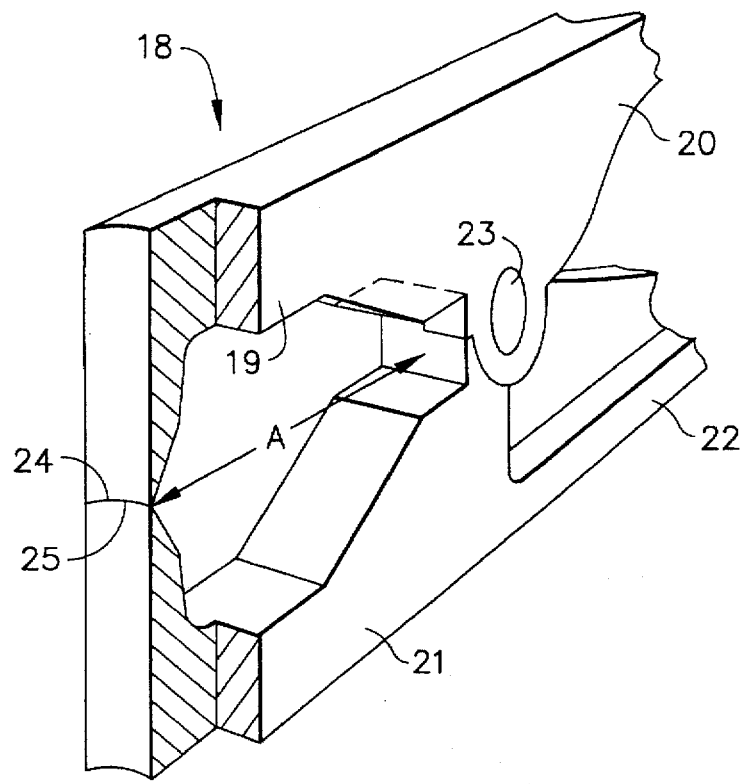
FIG. 10 is a fragmentary perspective view, partly in cross-section, of a concave nipper of the present invention.

A cross-shaped fixation plate is illustrated in FIG. 8 and is the result of the removal from the fixation plate 1 of FIG. 1 of fingers 4, 6, 8 and 10.

It will be evident to one skilled in the art that the exemplary plates illustrated in FIGS. 2 through 8 are but examples of many such plates which can be derived from plate 1 of FIG. 1. FIGS. 2 through 8 do clearly illustrate how various plate configurations can be obtained by removal of one or more selected ones of the fingers 3 through 10. Further configuring can be accomplished by removing segments of individual fingers. As is illustrated in FIG. 1, finger 7 could be shortened by cutting along broken line 16 or broken line 17. This can, of course, be done to any of fingers 3 through 10, and any length segment can be removed from a finger, depending upon the application for which the fixation plate is being prepared. Each of FIGS. 3 through 10 could be provided with indicia similar to lines 16 and 17 to assist the surgeon in cutting selected fingers to the appropriate length.

It will be understood that the fixation plates of the present invention can be used with any conventional surgical tools including surgical bending irons, surgical cutters, surgical pliers, surgical drills and drill guides, bone clamps, and various types of templates. Such surgical tools and instruments are well known in the art.

When removing one more of the fingers 3 through 10 from the hub 2, it is desirable that the cut edges be smooth, free of stress raisers, and generally continue the curved peripheral configuration of hub portion 2. To accomplish this, a nipper of the type shown in FIG. 10 may be provided. The nipper is generally indicated at 18 and comprises a first jaw portion 19 and a first handle portion 20 together with a second jaw portion 21 and a second handle portion 22. Jaw and handle portions 19–20 and jaw and handle portions 21–22 are pivoted together as at 23.

Jaw portions 19 and 21 provide cooperating, concave cutting edges 24 and 25, respectively. The concave cutting edges 24 and 25 may be so sized and shaped as to provide the smooth rounded peripheral surface of hub portion 2 at points where fingers are removed therefrom such as, for example, the peripheral surfaces 26 and 27 of FIG. 2. It will be understood that the distance indicated by arrow A between the rear wall of the jaw opening and the concave cutting edges 24 and 25 is preferably equal to or greater than the length of a finger so that the nipper 18 is capable of removing an entire finger.

It would also be preferred to provide a substantially identical nipper having concave cutting edges so sized and configured as to modify or trim the cuts 16 and 17 (see FIG. 1) when a portion is to be removed from an individual finger. The resulting arcuate cut will be smooth and free of stress raisers.

Figure 11:
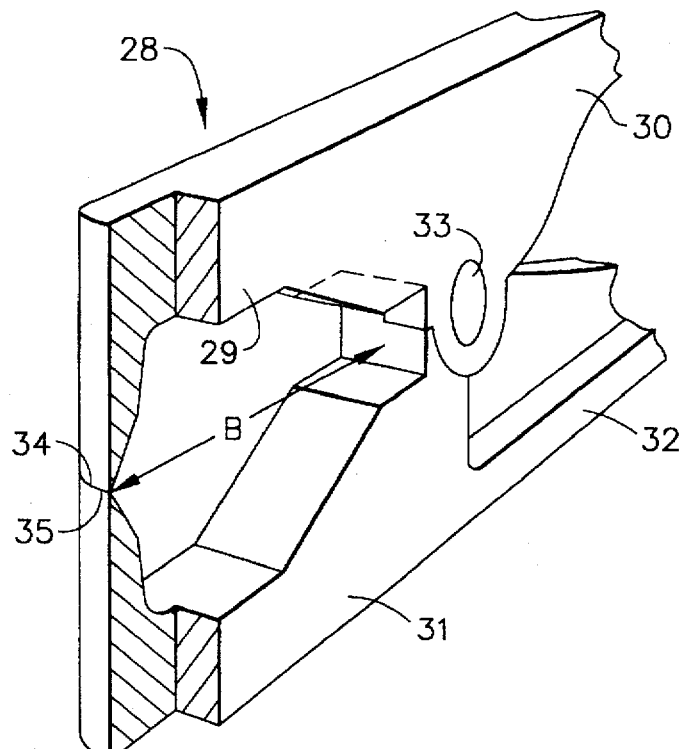
FIG. 11 is a fragmentary perspective view, partly in cross-section, of a convex nipper of the present invention.

FIG. 11 illustrates a nipper generally indicated at 28. The nipper 28 has a first jaw portion 29 and a first handle portion 30 and a second jaw portion 31 and a second handle portion 32. The jaw and handle portions 29–30 and the jaw and handle portions 31–32 are pivoted together as at 33. The tool 28 of FIG. 11 differs from the tool 18 of FIG. 10 primarily in that it is provided with a pair of convex cutting edges 34 and 35. Again it is preferred that the distance between cutting edges 34 and 35 and the rear wall of the jaw opening, as indicated by arrow B, be of a length equal to or greater than the length of a fixation plate finger. The convex cutting edges 34 and 35 are sized and shaped to trim or mofidy the curved edge portions 11 and 12 if required. It will be understood that nippers 18 and 28 could be of the double-acting type.

The fixation plate 1 of FIG. 1 could be provided with fingers which have scalloped rather than rectilinear longitudinal edges. Such a finger is illustrated at 36 in FIG. 9 constituting an integral part of a hub portion fragmentarily shown at 37. It will be understood that the hub portion 37 is identical to hub portion 2 of FIGS. 1 through 8. Fingers of the general shape of finger 36 are advantageous in that they require less material, are easier to bend and expose more of the adjacent bone or bone fragments, thereby promoting growth and healing.

Finally, it is within the scope of the present invention to make the fixation plate of FIG. 1 in a number of sizes. For most applications, it is believed that three sizes would be adequate. It would also be within the scope of the invention to make a diametric pair of fingers longer than the others. This is shown in FIG. 1 wherein fingers 4 and 8 (chosen arbitrarily) are shown extended in broken lines as at 4a and 8a with additional holes for surgical screws shown at 13a. Such a fixation plate would be particularly useful in the stabilization of a fractured or broken long bone such as a humerus, ulna, femur, tibia, or the like. If such an extending such an extended length finger is to be shortened or removed from the plate several cuts with nipper 18 will be required.

The internal fixation plate of the present invention having been described in detail, a few examples of its application will now be set forth. It will be understood by one skilled in the art that these examples are exemplary only.

Turning first to FIG. 12, this Figure comprises a partial, lateral view of the bone structure of the right foot of a patient. The foot is generally indicated at 38 with the talus shown at 39 and the calcaneus or heel bone shown at 40. FIG. 12 also partially shows the tibia 41 and fibula 42.

FIG. 12 illustrates a comminuted calcaneal fracture, with the fracture lines indicated at 43, 44 and 45.

FIG. 13 illustrates a fixation plate of the present invention applied to the calcaneus holding together the fragments of the comminuted heel bone. Comparing FIGS. 13 and 1, it will be noted that fingers 7 and 9 have been removed from the fixation plate hub portion 2. Fingers 3, 4 and 6 have been cut to appropriate length. Finger 10 has been bent to accommodate the top of the calcaneus. Each of the fingers has been bent to conform to the adjacent bone fragment. The fixation plate is affixed to the bone fragments by surgical screws 46.

FIG. 14 is a partial posterior view of the humerus 47 illustrating a comminuted intraarticular fracture of the elbow. The fracture lines are indicated at 48, 49 and 50. FIG. 15 illustrates a fixation plate of the present invention applied to the fracture of FIG. 14. A comparison of FIGS. 15 and 1 shows that fingers 6, 7, 9 and 10 have been removed from hub portion 2. Fingers 3, 4, 5 and 8, together with the hub portion 2, have been bent to conform to the adjacent bone or bone fragments. Fingers 4 and 5 are cut to length. The fixation plate has also been bent to accommodate the transepicondylar screw 51.

FIG. 16 is a partial posterior view of a femur 52 illustrating a T-fracture thereof at the knee. The fracture lines are shown at 53 and 54. FIG. 17 illustrates the application of a fixation plate of the present invention to the T-fracture of FIG. 16. The fixation plate is of the type illustrated in FIG. 4. It will be noted that the fixation plate is mounted by surgical screws, including three transepicondylar screws 55, 56 and 57. It will be further noted that finger 6 has been cut to length and the entire fixation plate has been bent to conform to the bone structure being repaired.

Modifications may be made in the invention without departing from the spirit of it.

What is claimed:

1. A multi-purpose internal universal fixation plate for the stabilization of fractured, broken and severed bones, said universal fixation plate comprising:

a central hub portion; and a plurality of pairs of diametrically disposed fingers extending substantially radially from said hub portion, wherein said universal fixation plate is made from a material capable of being cut and bent and is characterized adequate strength and biocompatability for use as an endo-implant; and whereby said universal fixation plate is capable of being cut into any one of a number of differently configured fixation plates by selectively removing all,portions of, one or more of said fingers, thus eliminating the necessity of maintaining a inventory of differently configured fixation plates.

2. The internal fixation plate claimed in claim 1 wherein said central hub portion is substantially circular and said fingers extend radially therefrom and are evenly spaced thereabout, said fingers comprising an integral one-piece part of said hub portion.

3. The internal fixation plate claimed in claim 2 wherein said fingers have perforations therealong for receipt of surgical screws by which said plate may be attached to the bone or bone fragments being stabilized.

4. The internal fixation plate claimed in claim 3 wherein said plate is made in more than one size.

5. The internal fixation plate claimed in claim 4 wherein said plate is made of material chosen from the class consisting of titanium, surgical grade stainless steel and surgical grade alloys.

6. The internal fixation plate claimed in claim 5 wherein said fingers have one of rectilinear and scalloped longitudinal sides and have rounded ends.

7. The internal fixation plate claimed in claim 6 wherein each of said fingers has one of round and elongated holes formed therein and spaced therealong for receipt of surgical screws by which said plate may be attached to the bone or bone fragment being stabilized.

8. The internal fixation plate claimed in claim 7 wherein said plate is adapted to have selected fingers removed to assume a shape chosen from the class consisting of a strap shape, a Y-shape, a skewed Y-shape, a T-shape, an L-shape, an H-shape and a cross shape.

9. The internal fixation plate claimed in claim 2 wherein said plate is made of any material capable of being cut and bent, characterized by adequate strength and characterized by compatibility for use as an endo-implant.

10. The internal fixation plate claimed in claim 9 wherein said plate is made of material chosen from the class consisting of titanium, surgical grade stainless steel and surgical grade alloys.

11. The internal fixation plate claimed in claim 9 wherein said plate is made of material chosen from the class consisting of titanium, surgical grade stainless steel, surgical grade alloys, and a material having said required characteristics and which is absorbable by the body.

12. The internal fixation plate claimed in claim 2 wherein said plate is made in more than one size.

13. The internal fixation plate claimed in claim 2 wherein said fingers narrow slightly in width at the junctures of the fingers and said hub portion.

14. The internal fixation plate claimed in claim 2 wherein said fingers have one of rectilinear and scalloped longitudinal sides and have rounded ends.

15. The internal fixation plate claimed in claim 2 wherein all of said fingers are of the same length.

16. The internal fixation plate claimed in claim 2 wherein all of said fingers save one diametric pair thereof are of the same length, said diametric pair of fingers being of a greater length.

17. The internal fixation plate claimed in claim 2 wherein said plate is initially planar prior to bending to shape.

18. The internal fixation plate claimed in claim 2 wherein each of said fingers has one of round and elongated holes formed therein and spaced therealong for receipt of surgical screws by which said plate may be attached to the bone or bone fragments being stabilized.

19. The internal fixation plate claimed in claim 2 wherein said fingers have transverse indicia formed thereon to guide the surgeon in cutting selected fingers to an appropriate length.

20. The internal fixation plate claimed in claim 2 wherein said plate is adapted to have selected fingers removed to assume a shape chosen from the class consisting of a strap shape, a Y-shape, a skewed Y-shape, a T-shape, an L-shape, an H-shape and a cross shape.

21. The internal fixation plate claimed in claim 1 wherein said fingers have perforations therealong for receipt of surgical screws by which said plate may be attached to the bone or bone fragments being stabilized.

22. The internal fixation plate claimed in claim 1 wherein said plate is made in more than one size.

23. The internal fixation plate claimed in claim 1 wherein said plate is made of material chosen from the class consisting of titanium, surgical grade stainless steel, surgical grade alloys, and a material having said required characteristics and which is absorbable by the body.

* * * * *

UNITED STATES PATENT AND TRADEMARK OFFICE
CERTIFICATE OF CORRECTION

PATENT NO. : 5,718,705
DATED : February 17, 1998
INVENTOR(S) : Giacomo J. Sammarco It is certified that error appears in the above-indentified patent and that said Letters Patent is hereby corrected as shown below:

In column 6, line 10, insert -- or -- after "all".

In column 6 line 12, insert -- large -- after "a".

In column 6, line 19, after "claim" delete "2" and insert -- 1 -- therefor.

Signed and Sealed this

Fifth Day of October, 1999

Attest:

Q. TODD DICKINSON

Attesting Officer  Acting Commissioner of Patents and Trademarks